US006458833B1

(12) United States Patent
Lu et al.

(10) Patent No.: US 6,458,833 B1
(45) Date of Patent: Oct. 1, 2002

(54) ORGANOMETALLIC COMPLEX

(75) Inventors: Kuang-Lieh Lu, Taipei (TW); Jih-Ru Hwu, Shin-Chu (TW); Shwu-Chen Tsay, Taipei (TW); Sheng-Fa Yu, Taoyuan (TW); Jui-Te Hung, Taipei (TW); Jiann-Jyh Huang, I-Lan County (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 09/989,768

(22) Filed: Nov. 20, 2001

(51) Int. Cl.$^7$ ..................... A61K 33/24; A61K 31/282; C07K 15/00
(52) U.S. Cl. ..................... 514/492; 514/184; 514/186; 514/188; 546/6; 546/8; 546/9; 546/10; 546/114
(58) Field of Search ............................ 546/6, 8, 9, 10; 514/184, 186, 188, 492

(56) References Cited

PUBLICATIONS

Davidson JL et al. J. Chem. Soc., Dalton Trans. (1983), (4), 783–6.*
Rudnicki et al. *Nicking Of Supercoiled DNA Via Metal Radicals Generated From Photolysis Of Species Containing Metal–Metal Bonds*. Bioorganic & Medicinal Chemistry Letters, vol. 1, No. 9, pp. 451–454, 1991.
Sherman et al. *Structural Aspects Of Platinum Anticancer Drug Interactions With DNA*. Chemical Reviews, vol. 87, No. 5, pp. 1153–1181, 1987.
Reedijk. *Improved Understanding in Platinum Antitumour Chemistry*. Chem. Commun., 1996, pp. 801–806.
Neenhold et al. *Major Groove Opening at the HIV–1 TAT–Binding Site of Tar RNA Evidenced By A Rhodium Probe*. Abstract Only. (Full Source: BioChemistry, vol. 34, No. 19, pp. 6303–6309, 1995.).
Reedijk. *The Relevance Of Hydrogen Bonding In The Mechanism Of Action Or Platinum Antitumor Compounds*. Inorganica Chemica Acta, 198–200 (1992), pp. 873–881.
Wong et al. *Current Status of Platinum–Based Antitumor Drugs*. Chemical Reviews, vol. 99, No. 9, pp. 2451–2466, 1999.

* cited by examiner

*Primary Examiner*—Evelyn Mei Huang
(74) *Attorney, Agent, or Firm*—Fish & Richardson P.C.

(57) ABSTRACT

A metal complex and its use for binding or cleaving a nucleic acid. The metal complex has the formula:

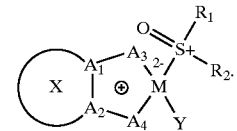

M is Pt, Pd, Ni, Co, or Cu; X is aryl, heteroaryl, cyclyl, or heterocyclyl; Y is halogen, tosylate, mesylate, triflate, pyrophosphate, or carboxylate; each of $A_1$ and $A_2$, independently, is N or C; each of $A_3$ and $A_4$, independently, is N, S, or O, wherein $A_1$, $A_2$, $A_3$, and $A_4$ taken together have one positive charge; and each of $R_1$ and $R_2$, independently, is alkyl, aryl, heteroaryl, alkoxyl, aryloxyl, heteroaryloxyl, alkoxylcarbonyl, aryloxylcarbonyl, or heteroaryloxylcarbonyl.

8 Claims, No Drawings

ORGANOMETALLIC COMPLEX

BACKGROUND

Transition metal complexes that can cleave DNA are widely known as "chemical nucleases." See, e.g., Pyle & Barton (1990) *Prog. Inorg. Chem.* 38: 413; Sigman et al. (1987) *Acc. Chem. Res.* 26: 98; and Stubbe & Kozarich (1987) *Chem. Rev.* 87: 1107. These complexes strongly bind to DNA and then cleave it under various conditions. For example, a transition metal complex can cleave DNA upon linking to a DNA-cleaving motif, e.g., acridine orange (Lippard et al. (1984) *J Am. Chem. Soc.* 106: 6102); upon X-ray irradiation (Grokhovsky & Zubarev (1991) *Nucl. Acids Res.* 19: 257); or under photolytic conditions (Rudnicki et al. (1991) *Bioorg. Med Chem. Lett.* 1: 451; or Thorp et al. (1995) *J Am. Chem. Soc.* 117:11673).

In addition, the just-described transition metal complexes may possess anticancer activity. See, e.g., Bruhn et al. (1987) *Prog. Inorg. Chem.* 38: 477; and Sherman & Lippard (1987) *Chem. Rev.* 87: 1153. For example, cisplatin and carboplatin (i.e., platinum complexes) have been routinely used for treating testicular and ovarian cancers (Christian (1992) *Semin. Oncol.* 19: 720; and Barnard (1989) *J Plat. Met. Rev.* 33: 162). In addition, many cisplatin derivatives have been developed as new anticancer reagents with less toxic side effect and reduced resistance. See Reedijk (1996) *J Chem. Soc., Chem. Commun.* 801; and Hambley (1997) *Coord. Chem. Rev.* 166: 181.

SUMMARY

This invention relates to a transition metal complex useful as a nucleic acid binding or cleaving agent.

In one aspect, this invention features a metal complex of the formula:

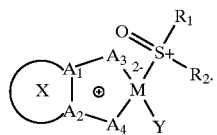

(I)

M is Pt, Pd, Ni, Co, or Cu; X (including atoms $A_1$ and $A_2$) is aryl, heteroaryl, cyclyl, or heterocyclyl; Y is halogen, tosylate, mesylate, triflate, pyrophosphate, or carboxylate; each of $A_1$ and $A_2$, independently, is N or C; each of $A_3$ and $A_4$, independently, is N, S, or O, wherein $A_1$, $A_2$, $A_3$, and $A_4$ taken together have one positive charge (a charge carried by one of the four atoms, e.g., $N^+$); and each of $R_1$ and $R_2$, independently, is alkyl, aryl, heteroaryl, alkoxyl, aryloxyl, heteroaryloxyl, alkoxylcarbonyl, aryloxylcarbonyl, or heteroaryloxylcarbonyl.

A subset of the metal complexes encompassed by the formula (I) is featured by that M is Pt. In these compounds, X is pyridinyl, one of $A_1$ and $A_2$ is N; Y is halogen; and each of $R_1$ and $R_2$, independently, is alkyl. One exemplary metal complex of this invention is PtCl(DMSO) [$\eta^2$-$C_5H_4SN(O)$]:

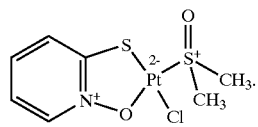

Alkyl, aryl, heteroaryl, cyclyl, heterocyclyl, alkoxyl, aryloxyl, heteroaryloxyl, alkoxylcarbonyl, aryloxylcarbonyl, or heteroaryloxylcarbonyl mentioned above refers to both substituted and unsubstituted moieties. As used herein, alkyl is a straight or branched hydrocarbon chain containing 1 to 6 carbon atoms. The term "substituted" refers to one or more substituents (which may be the same or different), each in replace of a hydrogen atom. Examples of substituents include, but are not limited to, halogen, hydroxyl, amino, cyano, nitro, $C_1$~$C_6$ alkyl, $C_1$~$C_6$ alkenyl, $C_1$~$C_6$ alkoxyl, aryl, heteroaryl, or heterocyclyl, wherein alkyl, alkenyl, alkoxyl, aryl, heteroaryl and heterocyclyl are optionally substituted with $C_1$~$C_6$ alkyl, aryl, heteroaryl, halogen, hydroxyl, amino, alkylamino, arylamino, dialkylamino, diarylamino, cyano, or nitro. The term "aryl" refers to a hydrocarbon ring system having at least one aromatic ring. Examples of aryl moieties include, but are not limited to, phenyl, naphthyl, and pyrenyl. The term "heteroaryl" refers to a hydrocarbon ring system having at least one aromatic ring which contains at least one heteroatom such as O, N, or S. Examples of heteroaryl moieties include, but are not limited to, pyridinyl, carbazolyl, and indolyl.

A salt of a metal complex of formula (I) is also within the scope of this invention. Such a salt, for example, can be formed between a positively charged substituent (e.g., sulfoxide) on the complex and an anion. Examples of an anion include fluoride, chloride, bromide, iodide, sulfate, sulfite, phosphate, acetate, oxalate, and succinate. Likewise, a negatively charged substituent can form a salt with a cation. Suitable cations include, but are not limited to, sodium ion, potassium ion, magnesium ion, calcium ion, and an ammonium cation such as teteramethylammonium ion.

This invention also features a method for binding or cleaving a nucleic acid. The method includes contacting the nucleic acid with one or more metal complexes described above. Cleavage of the nucleic acid can be achieved by UV irradiation of the metal complex-bound nucleic acid. The nucleic acid described herein refers to a purine-containing DNA or RNA. It can be single-stranded, double-stranded, or partially single-stranded and partially double-stranded. In some embodiments, the method of this invention is performed in an aqueous buffer having a pH value which ranges from 5 to 8. A cleavage can be carried out by using UV light having a wavelength>300 nm.

Other features, objects, and advantages of the invention will be apparent from the description and from the claims.

DETAILED DESCRIPTION

This invention relates to a transition metal complex and its use as a nucleic acid binding or cleaving agent. The metal complex of this invention can be prepared by well-known methods, including the synthetic routes disclosed herein.

For example, a metal complex can be prepared by adding a mercapto, oxide-substituted heteroaryl to a solution containing $K_2PtCl_4$. The addition is carried out in the dark. Subsequently, $R_1$, $R_2$-substituted sulfoxide is added to the solution to produce the desired metal complex. The product can be purified by column chromatography. Shown below is a scheme that depicts synthesis of a metal complex of this invention (e.g., complex 1, see the box in the scheme).

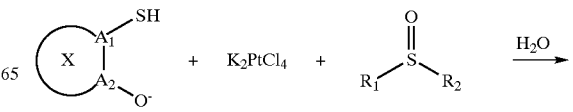

-continued

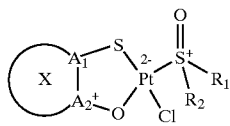

complex 1:
$R_1 = R_2$ = methyl;
$A_1$ = C; $A_2$ = N; and
X = pyridinyl

A transition metal complex of this invention can be used as a nucleic acid binding or cleaving agent. Typically, it binds to the heteroaryl ring of a purine on the nucleic acid. The binding can be coordination between the transition metal and a heteroatom, such as nitrogen. Take complex 1 for example. It specifically binds to the C-6 amino on an adenine. Without UV irradiation, a mass spectrometry analysis shows no sign of nucleic acid cleavage resulting from the binding. Upon UV irradiation, an intramolecular cyclization takes place, leading to nucleic acid cleavage. Moreover, the transition metal complex also targets a guanine in the presence of an external base (e.g., piperidine). Not only does the complex specifically bind to the C-2 amino on the guanine, a cleavage reaction also occurs with the assistance of the external base under UV irradiation. See the specific examples below.

A cleaved nucleic acid product (nicked nucleic acid) contains at least one break, wherein two adjacent bases are not covalently linked. It can be detected using denaturing polyacrylamide gels (Molecular Cloning, 2nd Ed. Sambrook et al. eds. Cold Spring Harbor Laboratory Press, 1989). Gel electrophoresis can also separate and detect a nicked nucleic acid which has been tagged with a fluorescent or radioactive label.

A transition metal complex of this invention can bind to and cleave a nucleic acid (e.g., DNA) in vivo. It is well known that selective interactions of a metal complex with cellular DNA result in death of tumor cells. For reviews, see Reedijk (1992) *Inorganica Chimica Acta* 198–200: 873; and Wong & Giandomenico (1999) *Chem Rev* 99: 2451. This invention, therefore, covers a pharmaceutical composition for treating tumor that contains an effective amount of at least one transition metal complex described in the "Summary" section and a pharmaceutical acceptable carrier. Also within the scope of this invention is a method of administering an effective amount of the complex to a subject in need of tumor treatment. "An effective amount" refers to the amount of the complex which is required to confer a therapeutic effect on the treated subject.

Further, the afore-mentioned transition metal complex can also serve as a nucleic acid scissors to produce short nucleic acid fragments. A variety of new techniques such as mass spectrometry and microarrays utilize short nucleic acid fragments in nucleic acid analysis or sequencing. See, e.g., Nordhoff (1996) *Trends Anal. Chem.* 15: 240; Ramsay (1998) *Nat. Biotechnol.* 16: 40; and Marshall & Hodgson (1998) *Nat. Biotechnol* 16: 27. Therefore, the transition metal complexes of this invention are useful for these new techniques. For example, the complex can be used in a gene chip for detecting cancer or virus diseases.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

Synthesis of Organoplatinum Complex PtCl(DMSO)[$\eta^2$-$C_5H_4SN(O)$]

To a solution of sodium 2-mercaptopyridine N-oxide in N,N-dimethylformamide (10 mL), $K_2PtCl_4$ (415 mg, 1.00 mmol) in 100 mL aqueous solution was slowly added within 1.0 h in the dark. Subsequently, dimethyl sulfoxide (DMSO, 1.0 mL) was added into the solution and stirred for 3 days. The solvents in the solution were removed under reduced pressure and a product was obtained. The product was purified by using column chromatography packed with silica gel (100% $CH_2Cl_2$ as eluant) to produce [Pt(Cl)(DMSO)($\eta^2$-$C_5H_4SN(O)$)] (complex 1) as yellow powder (408 mg, 0.940 mmol, 94% yield).

Elemental Analysis for $PtC_7H_{10}NO_2S_2$: Calculated: C, 19.34; H, 2.32; N, 3.22. Found: C, 19.56; H, 2.18; N, 3.10.

MS (FAB, $^{195}$Pt, $^{37}$Cl) m/z: 436 (M$^+$), 399 (M$^+$–Cl), 305 (M$^+$–L).

Crystallographic data: two molecules composed the unit cell, $C_{14}H_{20}C_{12}N_2O_4S_4Pt_2$:

M=869.64, triclinic, space group P1, the lattice constants a =10.249 (3) Å, b=10.963 (5) Å, c=11.083 (3) Å, $\alpha$=82.71(3)°, $\beta$=76.183(21)°, $\gamma$=76.64(3)°, V=1171.1(7) Å$^3$, Z=2, Dc=2.462 g cm$^{-3}$, T=298 K, $\lambda$=0.71069 Å, $\mu$ (Mo/Ka)=12.6336 nm$^{-1}$, Enraf-nonius CAD4-diffractometer, $2\theta_{max}$=45.0°, 3259 refections measured, 1861 were considered observed (R=0.057, $\omega$R (F$^2$)=0.059).

The [Pt(Cl)(DMSO)($\eta^2$-$C_5H_4SN(O)$)] structure was also identified by single crystal X-ray diffraction analysis. The 1-hydroxypyridine-2-thione donated three electrons in total to coordinate with a Pt metal atom, i.e., the thiolate center contributed one electron and the oxygen atom offered two electrons.

Single-strand DNA Cleavage

Cleavage at various pH's: A reaction mixture (10 $\mu$L) containing supercoiled circular $\phi$X174 RFI DNA stock solution (50 $\mu$M/base pair), complex 1 (5.0 $\mu$M), and a phosphate buffer (0.10 M, pH 5.0, 6.0, 7.0, and 8.0) in a Pyrex vial was preincubated at 37° C. The reaction mixture was then irradiated with 350 nm UV light (32-W) for 2.0 h at room temperature. After adding a gel-loading buffer (0.25% bomophenol blue, 0.25% xylene cyanol, and 30% glycerol), the reaction mixture was loaded on a 1% agarose gel, followed by ethidium bromide staining. The gel was visualized by a 312-nm UV transilluminator and photographed by a FB-PDC-34 camera. Supercoiled circular DNA and cleaved DNA were clearly seen from the gel. The results showed that only cleaved DNA was observed when the reaction mixture had a pH of 5.0, 6.0, or 7.0, and both supercoiled circular DNA and cleaved DNA were observed when the reaction mixture had a pH of 8.0.

Cleavage at various complex concentrations: A reaction mixtures (10 $\mu$L) containing supercoiled circular $\phi$X174 RFI DNA stock solution (50 $\mu$M/base pair), complex 1 (0.050–100 $\mu$M), and a phosphate buffer (0.10 M, pH 6.0) in a Pyrex vial was preincubated at 37° C. The mixture was irradiated with 350 nm UV light (32-W) for 2.0 h at room temperature. After adding a gel-loading buffer (0.25% bromophenol blue, 0.25% xylene cyanol, and 30% glycerol), the reaction mixture was loaded on a 1% agarose gel, followed by ethidium bromide staining. The gel was visualized by a 312-nm UV transilluminator and photographed by a FB-PDC-34 camera. Supercoiled circular DNA (form I) and cleaved DNA (form II) were clearly seen from the gel.

The results are summarized in Table 1:

TABLE 1

Single-strand supercoiled circular φX174 RFI cleavage with complex 1

| complex | concentration (μM) | (% form I) | (% form II) | (% form II)/ (% form I) |
|---|---|---|---|---|
| none | — | 91 | 9.0 | 0.10 |
| 1[a] | 500 | 93 | 7.0 | 0.070 |
| 1 | 5.0 | 7.1 | 93 | 13 |
| 1 | 2.5 | 20 | 80 | 4.0 |
| 1 | 1.0 | 37 | 63 | 1.7 |

[a]In the dark.

The results showed that complex 1 cleaved DNA in a pH-dependent manner (pH 5.0–8.0), and favored acidic conditions (pH 5.0–7.0). Unexpectedly, this metal complex exhibited very strong DNA cleaving activity even at a concentration as low as 1.0 μM. Furthermore, the cleavage of single-strand DNA did not occur in the dark.

Site-Specific DNA Cleavage

A 160-bp dsDNA fragment was prepared from the 501–660 fragment of pBR322 DNA. It was amplified by the polymerase chain reaction (Bailly & Waring (1995) *J Am. Chem. Soc.* 117: 7311; Bailly et al. (1993) *J Am. Chem. Soc.* 115: 3784; and Sayers & Waring (1993) *Biochemistry* 32: 9094), and labeled at the 5'-terminus with γ-[$^{32}$P]-ATP and T4 polynucleotide kinase. A reaction mixture containing a 5'-terminus labeled $^{32}$P-DNA solution, a phosphate buffer (0.10 M, pH 6.0), and complex 1 (20–100 μM) in a Pyrex vial was preincubated at 37° C. for 30 min. The reaction mixture was irradiated with 350-nm UV light under aerobic conditions for 2.0 h at room temperature. The bound metal complexes on DNA fragments were removed by using 0.30 N NaCN (pH=11) at 37° C. for 8.0 h (Schwartz et al. (1990) *J Am. Chem. Soc.* 112: 3673; and Zou et al. (1994) *Biochemistry* 33: 5404). The reaction mixture was then quenched with either a gel-loading buffer or 95% ethanol. Some samples subjected to piperidine treatment were precipitated by addition of ethanol and resuspended in an aqueous piperidine solution (1.0 M, 60 μL) at 95° C. for 30 min. Subsequently, all samples were sequentially lyophilized, treated with water (30 μL), lyophilized, and resuspended in a gel-loading buffer (80% foramide, 0.25% bromophenol blue, and 0.25% xylene cyanol). The samples and the Maxam-Gilbert markers were analyzed using 10% polyacrylamide/8.0 M urea gel. The electrophoresis was performed at a voltage of 300 V for 60 min and raised to 600 V for another 8.0 h. The gel was visualized using Kodak X-Omat Ar-5 film in an intensifying screen, which was exposed at −70° C. for 24 h. Quantitation of relative intensities of DNA fragments was performed using a Microtek scanner and NIH 1.60 image program.

The detected DNA fragments were compared with Maxam-Gilbert markers on an autoradiogram, and quantitated by a computer-assisted program. The results showed that complex 1 cleaved DNA at purine residues with hot piperidine treatment (Armitage (1998) *Chem. Rev.* 98: 1171) and at adenine residues without piperidine treatment.

DNA Binding and Cleaving Mechanisms

A double helical oligonucleotide d(ATAT)$_2$ was prepared and added to a phosphate buffer solution (pH=6.0) containing complex 1 (1:1). The solution was kept in the dark for 2.0 h. An intermediate was detected, at a yield of 57%, with a signal at 650.1 for (M+H$^+$) as analyzed by an electron spray ionization detector in LC-mass chromatogram. Then, the solution was irradiated with 350 nm-UV light for 2.0 h at room temperature. A product was detected with a signal at 456.1 for (M+H$^+$). The results indicated that complex 1 first bound to the C-6 amino on an adenine to form the intermediate. Then an intramolecular cyclization took place to remove the DMSO and to form a covalent bond between the N-7 nitrogen atom and the platinum in complex 1, resulting in the oligonucleotide cleavage. The control experiment showed that the cleavage reaction was triggered by the UV irradiation.

The scheme below depicts the just-described reaction:

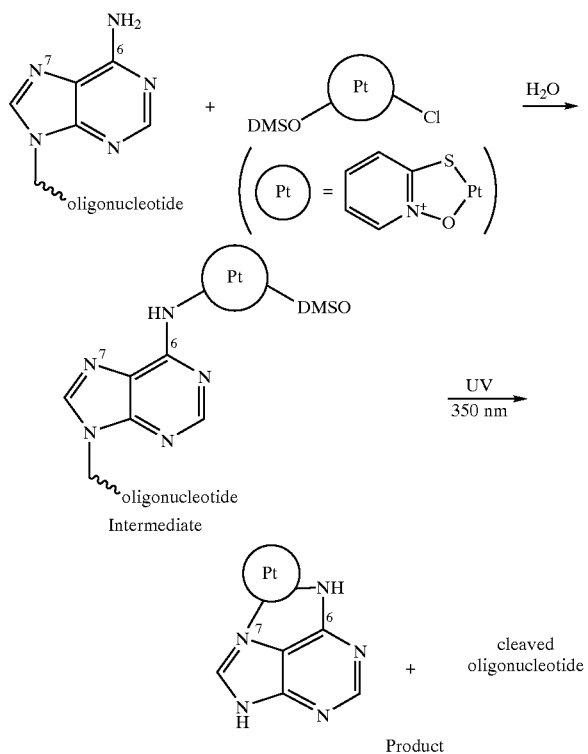

As a comparison, a reaction involving 2'-deoxyguanosine and complex 1 was carried out. Complex 1 bound to the C-2 amino on a guanine to form a Pt-N covalent bond. An intramolecular cyclization did not occur due to the distance and geometrical disfavor between the Pt and the N-7 nitrogen atom of guanine. As a result, cleavage at a guanine site required assistance from an external base (e.g., piperidine). In another experiment, an excess of complex 1 was added to a 2'-deoxyguanosine solution, followed by piperidine treatment. An intermediate was detected, at a yield of 42%, with a signal at 1063.9 for (M+H$^+$) as analyzed by an electron spray ionization detector in LC-mass chromatogram. The intermediate was able to give a cyclization product, at a yield of 80%, with a signal at 792.0 for (M+H$^+$) upon 350-nm UV light irradiation, but not in the dark. The scheme below depicts the just-described reaction:

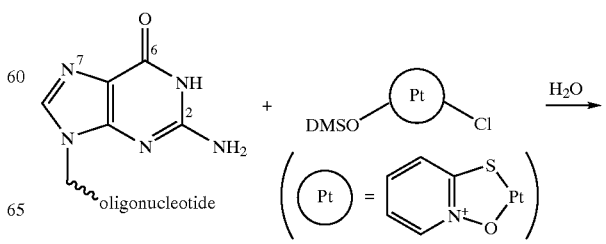

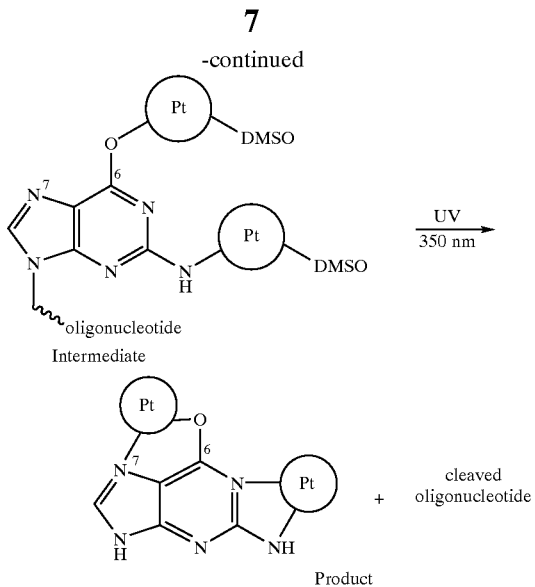

The above results indicated that complex 1 was an efficient DNA binder or potent cleaver under control conditions; and UV light functioned as a trigger to initiate the cleavage at the purine residues.

OTHER EMBODIMENTS

All of the features disclosed in this specification may be combined in any combination. Each feature disclosed in this specification may be replace by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Accordingly, other embodiments are also within the scope of the following claims.

What is claimed is:

1. A metal complex of the formula:

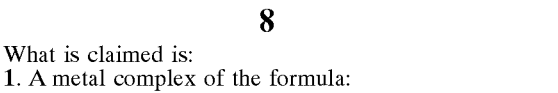

wherein
M is Pt;
X is pyridinyl;
Y is halogen, tosylate, mesylate, triflate, pyrophosphate, or carboxylate;
$A_1$ is C, $A_2$ is N, $A_3$ is S, and $A_4$ is O, wherein $A_1$, $A_2$, $A_3$, and $A_4$ taken together have one positive charge; and
each of $R_1$ and $R_2$, independently, is alkyl, aryl, heteroaryl, alkoxyl, aryloxyl, heteroaryloxyl, alkoxylcarbonyl, aryloxylcarbonyl, or heteroaryloxylcarbonyl.

2. The metal complex of claim 1, wherein Y is halogen.

3. The metal complex of claim 1, wherein each of $R_1$ and $R_2$ is alkyl.

4. The metal complex of claim 1, wherein the metal complex is of the formula:

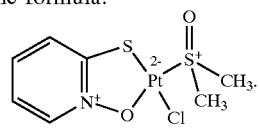

5. A method of binding or cleaving a nucleic acid, comprising contacting the nucleic acid with a metal complex of claim 1 in an amount effective for binding or cleaving a nucleic acid.

6. The method of claim 5, wherein Y is halogen.

7. The method of claim 5, wherein each of $R_1$ and $R_2$ is alkyl.

8. A method of claim 5, wherein the metal complex is of the following formula:

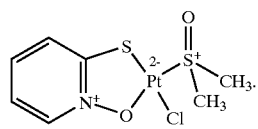

* * * * *